(12) United States Patent
Liu (10) Patent No.: US 9,497,996 B2
(45) Date of Patent: *Nov. 22, 2016

(54) ELECTRONIC CIGARETTE

(71) Applicant: Qiuming Liu, Shenzhen, Guangdong Province (CN)

(72) Inventor: Qiuming Liu, Shenzhen, Guangdong Province (CN)

(73) Assignee: HUIZHOU KIMREE TECHNOLOGY CO., LTD., SHENZHEN BRANCH, Shenzhen, Guangdong Province (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/185,919

(22) Filed: Feb. 20, 2014

(65) Prior Publication Data

US 2014/0360516 A1 Dec. 11, 2014

Related U.S. Application Data

(63) Continuation-in-part of application No. PCT/CN2013/076902, filed on Jun. 7, 2013.

(51) Int. Cl.
*A24F 47/00* (2006.01)
*A61M 15/06* (2006.01)

(52) U.S. Cl.
CPC ............ *A24F 47/008* (2013.01); *A61M 15/06* (2013.01)

(58) Field of Classification Search
CPC .................... A24F 47/00; A24F 47/002; A24F 47/004; A24F 47/006; A24F 47/008; A61M 15/06

See application file for complete search history.

(56) References Cited

FOREIGN PATENT DOCUMENTS

| CN | 101627837 A | * | 1/2010 | ............ A24F 47/00 |
| CN | 202566289 U | * | 12/2012 | ............ A24F 47/00 |
| WO | PCT/CN2013/076902 | | 6/2013 | |

\* cited by examiner

*Primary Examiner* — Anthony Calandra
(74) *Attorney, Agent, or Firm* — Cheng-Ju Chiang (57) ABSTRACT

An electronic cigarette of the invention includes an atomizing device for vaporizing cigarette liquid, a battery which is electrically connected with and supply power to the atomizing device, and a first electrode assembly set between the battery and the atomizing device. Herein, the first electrode assembly includes an electrode seat, an electrode and a resilient mechanism. The electrode seat is electrically connected with the battery, the electrode resiliently connects electrode of the atomizing device, and the resilient mechanism is resiliently connected between the electrode seat and the electrode. The electronic cigarette of the embodiments has resilient electrode assembly, simple structure, and high liability of electric circuit connection.

16 Claims, 6 Drawing Sheets

FIG. 7

ELECTRONIC CIGARETTE

BACKGROUND OF THE INVENTION

1. Field of the Invention

The present invention relates to an electronic cigarette field, and particularly to an electronic cigarette equipped with a simple and resilient electrode assembly.

2. Related Art

In the existing electronic cigarette, the electrode assembly for electrically connecting the atomizing device and the corresponding battery electrode consists of mutually insulated connecting seat and pole; the pole is configured as an independent component, and is tightly fitted in center of the connecting seat by means of an insulation sleeve; the atomizing device and the battery contact by means of directly abutting, while the connection therebetween has poor reliability.

SUMMARY OF THE INVENTION

An object of the present invention is to provide an electronic cigarette, which facilitates manufacturing and assembly of the same, and of which electric circuit connection is reliable.

To achieve the above object, an electronic cigarette is provided in the present invention, comprising an atomizing device for vaporizing cigarette liquid, a battery electrically connected with and supplying electricity to the atomizing device, and a first electrode assembly disposed between the battery and the atomizing device; herein, the first electrode assembly comprises a first electrode seat, a first electrode and a resilient mechanism; the first electrode seat is electrically connected with the battery; the first electrode resiliently engaged with the atomizing device by means of the resilient mechanism, and the resilient mechanism is resiliently connected between the electrode seat and the electrode.

Furthermore, the first electrode seat defines a cavity, the first electrode is set in an open end of the cavity, the open end inwards and radially extends to form an interior baffle ring; one end of the electrode disposed in the cavity radially and outwards extends to form an exterior baffle ring engaged with the interior baffle ring, and the other end thereof extending outwards from the cavity under an action of the resilient mechanism.

Furthermore, either end of the resilient mechanism are respectively fixed and electrically connected with the first electrode seat and the first electrode.

Furthermore, the resilient mechanism is a compressible spring or spring plate electrically connected with the first electrode seat and the first electrode.

Furthermore, the resilient mechanism is configured as two mutually-repelled magnets respectively disposed at the first electrode seat and the first electrode.

Furthermore, the resilient mechanism is an airbag.

Furthermore, the first electrode seat and the first electrode respectively define a first air inlet vent and a second air inlet vent for communicating an air passage.

Furthermore, the electronic cigarette comprises a main rod, the first electrode assembly is mounted within the main rod by means of a first connecting seat; the first connecting seat centrally defines a first electrode chamber which longitudinally runs through from its top to bottom end; the first electrode assembly is tightly fitted in the first electrode chamber via a first insulation sleeve; and the first connecting seat is made from conductive material and is insulated from the first electrode assembly.

Furthermore, the atomizing device has an electric heating wire; and a second electrode which is resiliently contacted by the first electrode, is disposed at an end of the atomizing device opposite to the battery.

Furthermore, the second electrode is fixed in the main rod by means of a second connecting seat; the second connecting seat centrally defines a second electrode chamber which longitudinally runs through its top to bottom end; the second electrode is tightly fitted in the second electrode chamber by means of a second insulation sleeve; the second connecting seat is made from conductive material; the second electrode and the second connecting seat are insulated from each other, and respectively connected with either end of the electric heating wire to form positive and negative electrodes of the atomizing device.

Furthermore, one end of the first connecting seat facing the second connecting seat is configured as a fixing groove for receiving a corresponding end of the second connecting seat, and the end of the second connecting seat inserted in the first connecting seat forms an extension adapted for an interior profile of the fixing groove whereby being received in the fixing groove.

Furthermore, the main rod comprises a power rod and an inhaling rod interconnected; the battery is set in the power rod, the atomizing device is set in the inhaling rod, the first connecting seat is set in one end of the power rod where the inhaling rod is interconnected, the second connecting seat is set in one end of the inhaling rod where the power rod is interconnected.

Furthermore, the power rod and the inhaling rod is magnetically connected, the power rod is provided with a first magnetic part where the inhaling rod is connected, the inhaling rod is correspondingly provided with a second magnetic part for magnetically attracting the first magnetic part whereby to tightly connect the power rod.

Furthermore, the first connecting seat is made from magnet or magnetic material to form the first magnetic part, or the corresponding end of the power rod is provided with an independent component made from conductive magnet or magnetic material to form the first magnetic part; the second connecting seat is made from magnet or magnetic material to form the second magnetic part, or the corresponding end of the inhaling rod is provided with an independent component made from conductive magnet or magnetic material to form the second magnetic part.

Furthermore, the first magnetic part is a permanent magnet; a flange is formed where the first electrode chamber is joined with the fixing groove, the permanent magnet abuts against the flange via the first insulated sleeve and is insulated from the first electrode assembly.

The present invention has the advantages as: the electrode assembly comprises the electrode seat and the electrode both of which are resiliently connected with each other; therefore, the positive and negative electrodes of the atomizing device are resiliently engaged with the positive and negative poles of the battery, which is simple in structure, convenient for assembly, and liable for connection.

Embodiments of the present invention will now be described, with reference to the attached Figures, wherein:

DESCRIPTION OF THE PREFERRED EMBODIMENTS

Referring to FIGS. 1 to 7, the present invention is to provide an electronic cigarette; comprising an atomizing device 10 for vaporizing cigarette liquid into aerosol, and a battery 20 electrically connected with and supplying power to the atomizing device 10.

Figure 3:
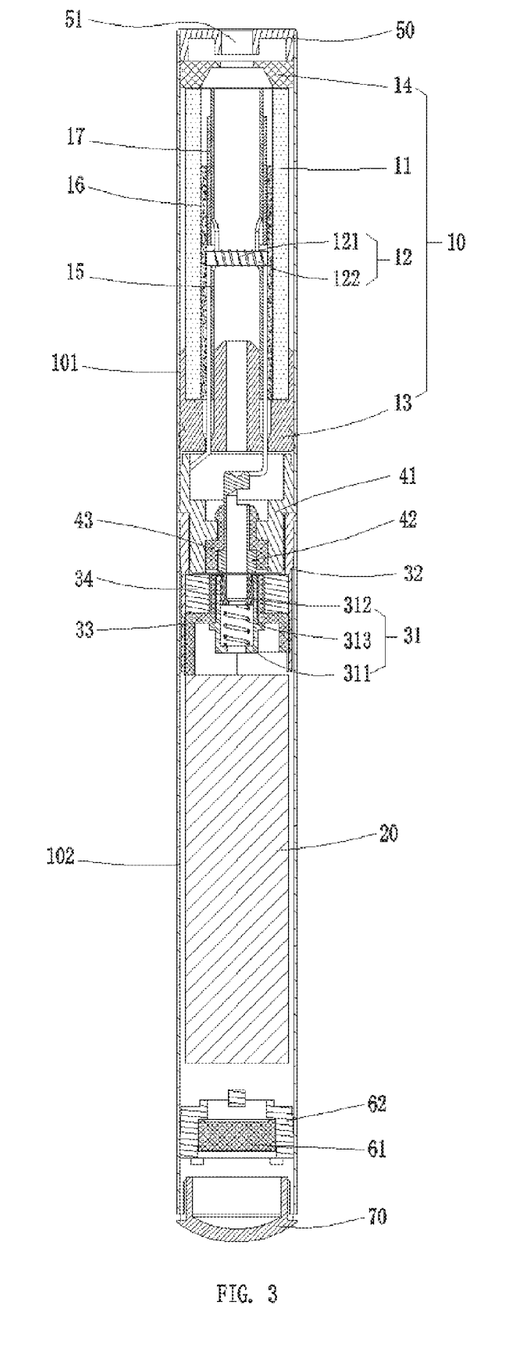
FIG. 3 is a cross-sectional view of the electronic cigarette in accordance with the embodiment of the present invention.

As shown in FIG. 3, a first electrode assembly 31 is provided between the battery 20 and the atomizing device 10; the first electrode assembly 31 is used for electrically connected the battery 20 with the atomizing device 10 so as for electric connection of the circuit.

The first electrode assembly 31 comprises an electrode seat 311, an electrode 312 and a resilient mechanism 313. Both the electrode seat 311 and the electrode 312 are made from conductive metal materials. The electrode seat 311 is electrically connected with the battery 20, the electrode 312 resiliently contacts the electrode of the atomizing device 10, and the resilient mechanism 313 is resiliently connected between the electrode seat 311 and the electrode 312. The electrode seat 311 and electrode 312 respectively define a first air inlet vent 3111 and a second air inlet vent 3121 for intercommunicating the air passage.

Figure 5:
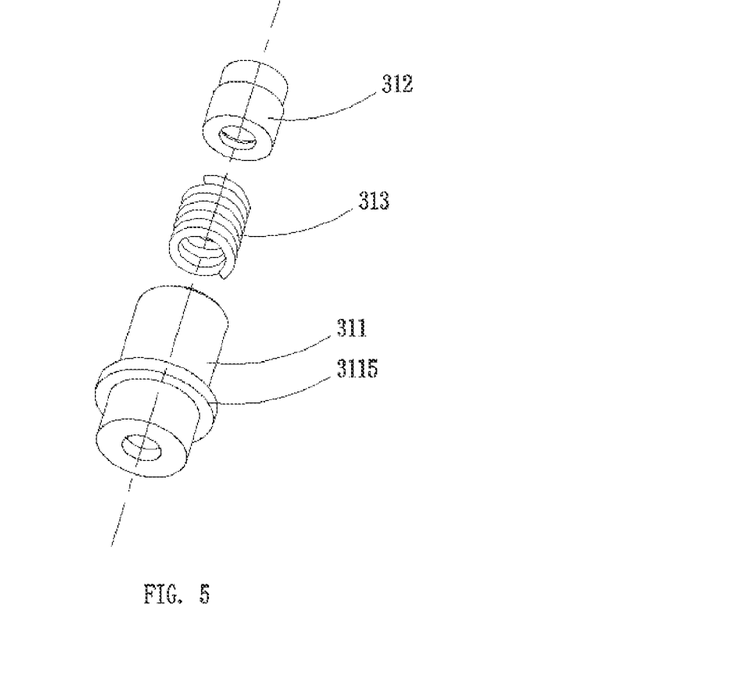
FIG. 5 is an exploded and perspective view of a first electrode assembly of the electronic cigarette in accordance with the embodiment of the present invention.
Figure 6:
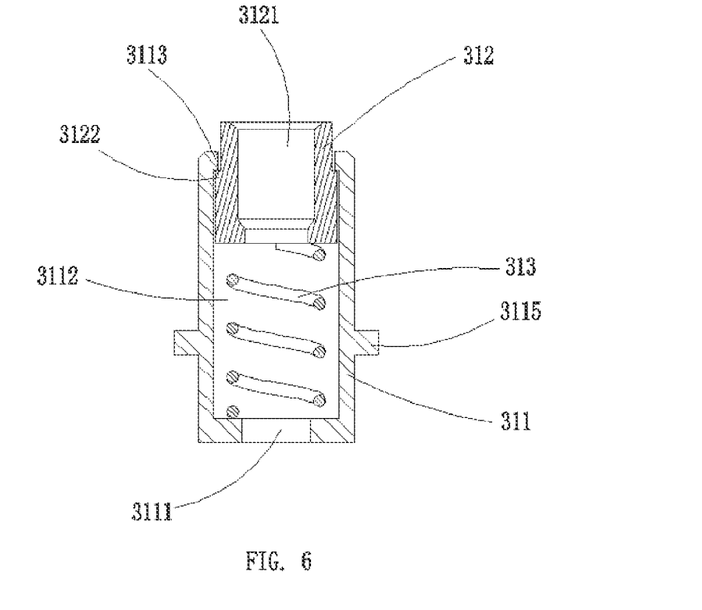
FIG. 6 is a cross-sectional view of the first electrode assembly of the electronic cigarette in accordance with the embodiment of the present invention.

Referring to FIG. 5 and FIG. 6, as a preferable embodiment, the electrode seat 311 centrally defines a cavity 3112, and the electrode 312 is resiliently fitted in an open end (namely a top end) of the cavity 3112 by the resilient mechanism 313. The top open end of the cavity 3112 radially extends inwards to form an interior baffle ring 3113; a bottom end of the electrode 312 disposed in the cavity 3112, radially extends outwards and forms an exterior baffle ring 3122 to be engaged with the interior baffle ring 3113; and a top end of the electrode 312 axially and movably extends out of the cavity 3112 under the resilient action of the resilient mechanism 313 at its bottom end, while is limited by means of the engagement between the interior and exterior baffle rings 3113, 3122. The electrode seat 311 substantially is a hollow cylinder which exteriorly and radially forms an annular flange 3115 therearound.

Before assembly, the width of the open end of the cavity 3112 is the same as the width of the cavity 3112; during assembly, the resilient mechanism 313 and the electrode 312 are successively placed into the cavity 3112; thereafter, the open end of the cavity 3112 is pressed by means of cold pressing device or the like devices to form the interior baffle ring 3113 for sealing and stopping the electrode 312.

As another embodiment, it is not necessary to set such interconnected structure as the interior baffle ring 3113 engaged with the exterior baffle ring 3122 between the electrode seat 311 and the electrode 312, while both ends of the resilient mechanism 313 are directly, respectively and fixedly engaged with the electrode seat 311 and the electrode 312, and the electrode seat 311 and the electrode 312 keep electrically connected. Namely, the resilient mechanism 313 may be directly and resiliently engaged between the electrode seat 311 and the electrode 312; or, both ends of the resilient mechanism 313 can be fixedly connected between the electrode seat 311 and the electrode 312 by means of fixed connection means such as welding connection, clamping connection, and etc.

As shown in FIG. 6, in accordance with the embodiment, the resilient mechanism 313 is preferably configured as a compressible spring electrically connected with both the electrode seat 311 and the electrode 312. It is understood that the resilient mechanism 313 can also be configured as a spring plate electrically connected with both the electrode seat 311 and the electrode 312; or, the resilient mechanism 313 can also be configured as two magnets repelling each other on the electrode seat 311 and the electrode 312; or, the resilient mechanism 313 can also be configured as an airbag.

Figure 1:
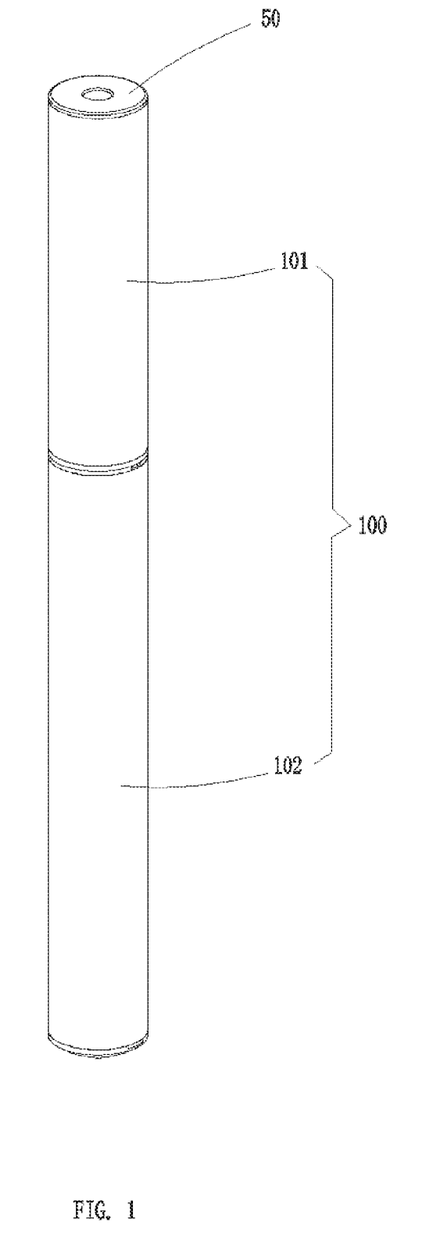
FIG. 1 is a perspective view of an electronic cigarette in accordance with an embodiment of the present invention.
Figure 2:
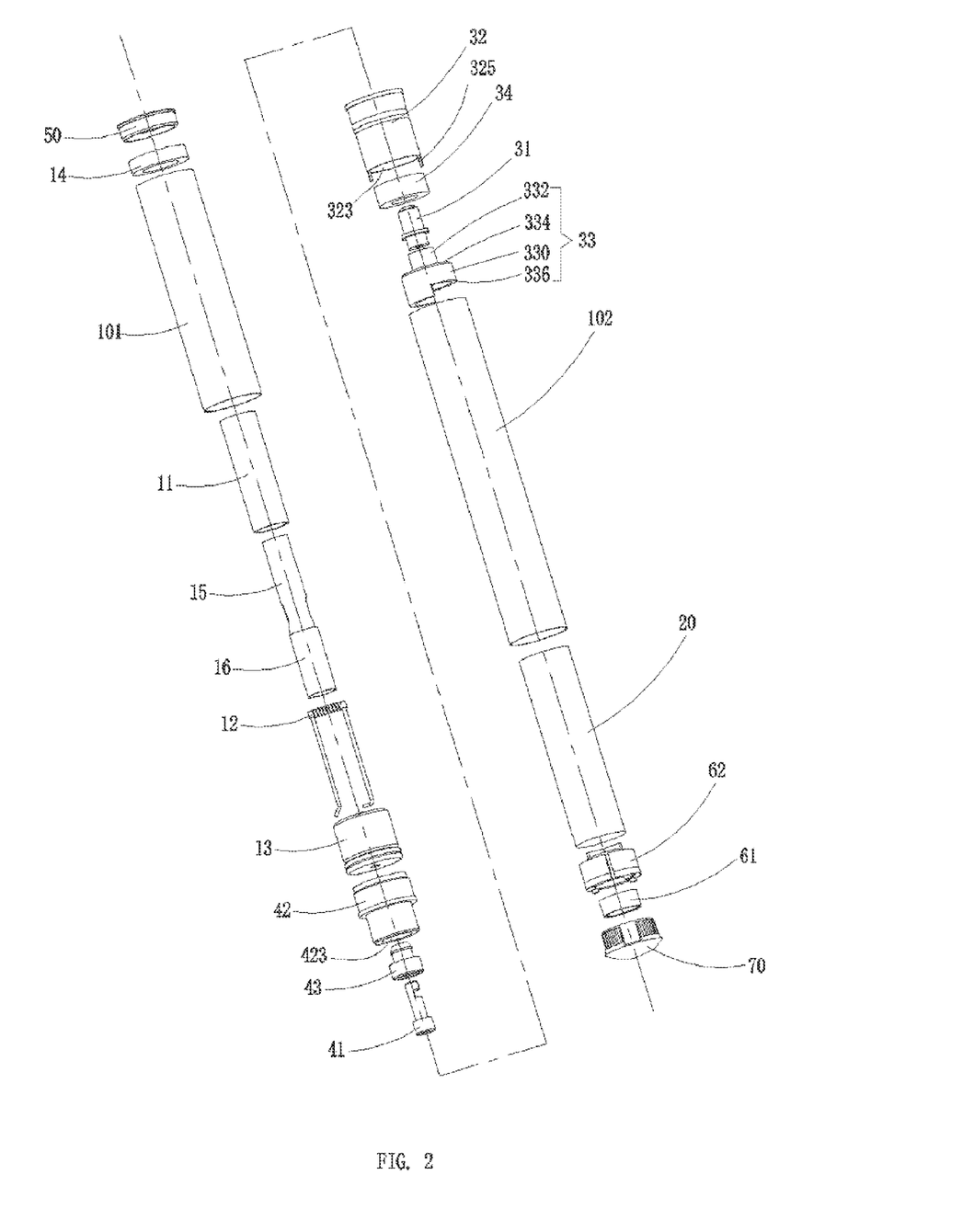
FIG. 2 is an exploded and perspective view of the electronic cigarette in accordance with the embodiment of the present invention.
Figure 4:
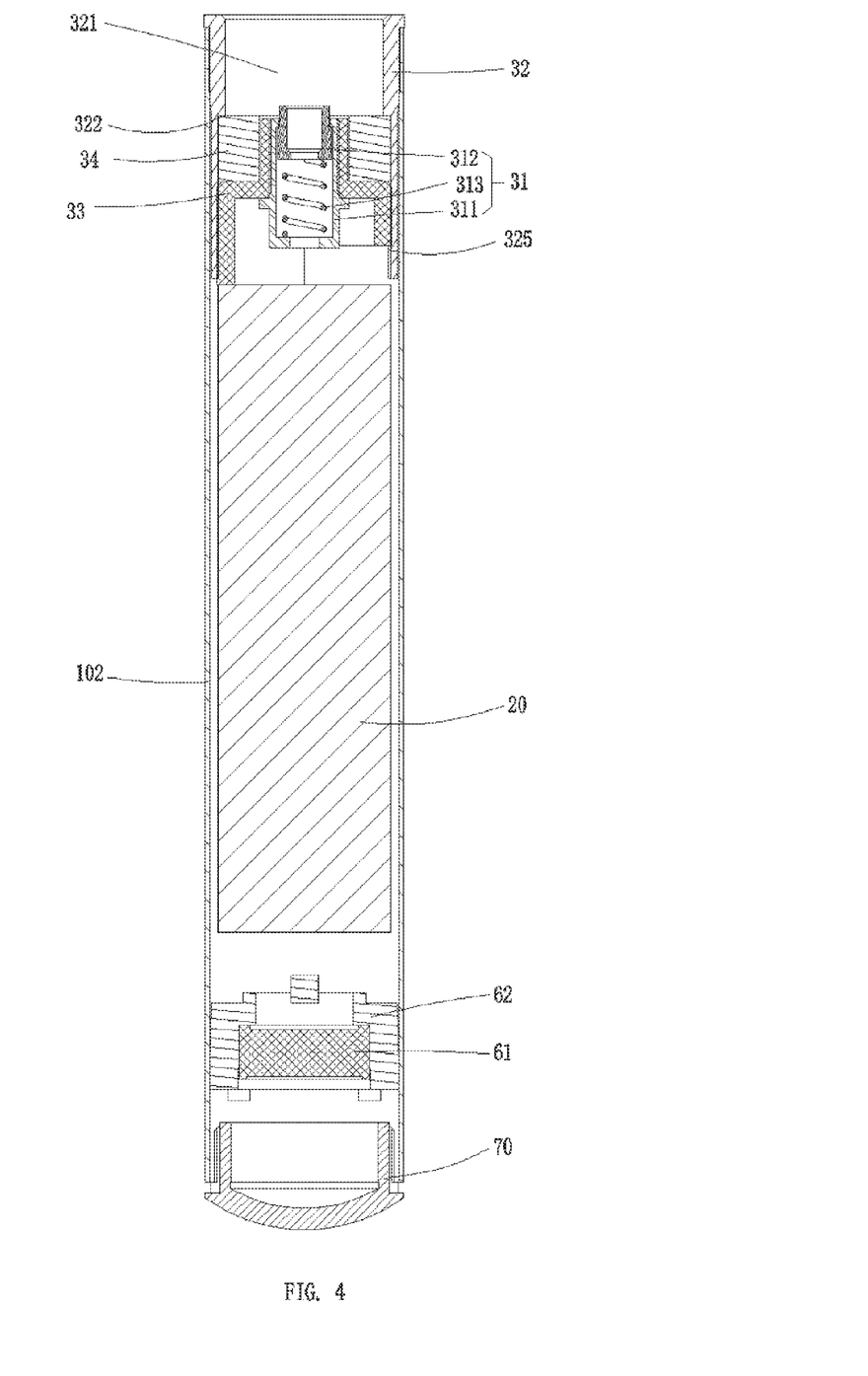
FIG. 4 is a cross-sectional view of a power rod of the electronic cigarette in accordance with the embodiment of the present invention.

Referring to FIG. 2 to FIG. 4, in accordance with this embodiment, the electronic cigarette further comprises an exterior housing as a main rod 100 (labeled in FIG. 1) encasing the atomizing device 10 and the battery 20 therein, the first electrode assembly 31 is mounted in the main rod 100 by means of a first connecting seat 32. The first connecting seat 32 is made from conductive materials, is substantially shaped as a hollow cylinder axially with an extending flange 325 from its bottom end, and at its center defines a first electrode chamber 323 which longitudinally runs through from its top to bottom end. The first electrode assembly 31 is tightly fitted within the connecting seat 32 and is located in the first electrode chamber 323 via a first insulation sleeve 33, and meanwhile is insulated from the first connecting seat 32 via the first insulation sleeve 33. The first insulation sleeve 33 comprises a substantially hollow cylindrical base 330. The cylindrical base 330 at its top wall 334 coaxially forms a hollow cylindrical extension 332 with relatively smaller diameter than the cylindrical base 330. Additionally, the hollow cylindrical base 330 defines a cutout 336. The extending flange 325 of the first connecting seat 32 is adapted for and engaged with the peripheral edge of cutout 336. The electrode seat 311 is fixed within the first insulation sleeve 33 in such way that its top section is tightly fitted in the hollow cylindrical extension 332 of the insulation sleeve 33 with its annular flange 3115 abutting under the top wall 334 of the cylindrical base 330. The first insulation sleeve 33 is tightly fitted within the bottom end of the first connecting seat 32 further with the peripheral edge of the cutout 336 stopped on the extending flange 325 of the first connecting seat 32.

Figure 7:
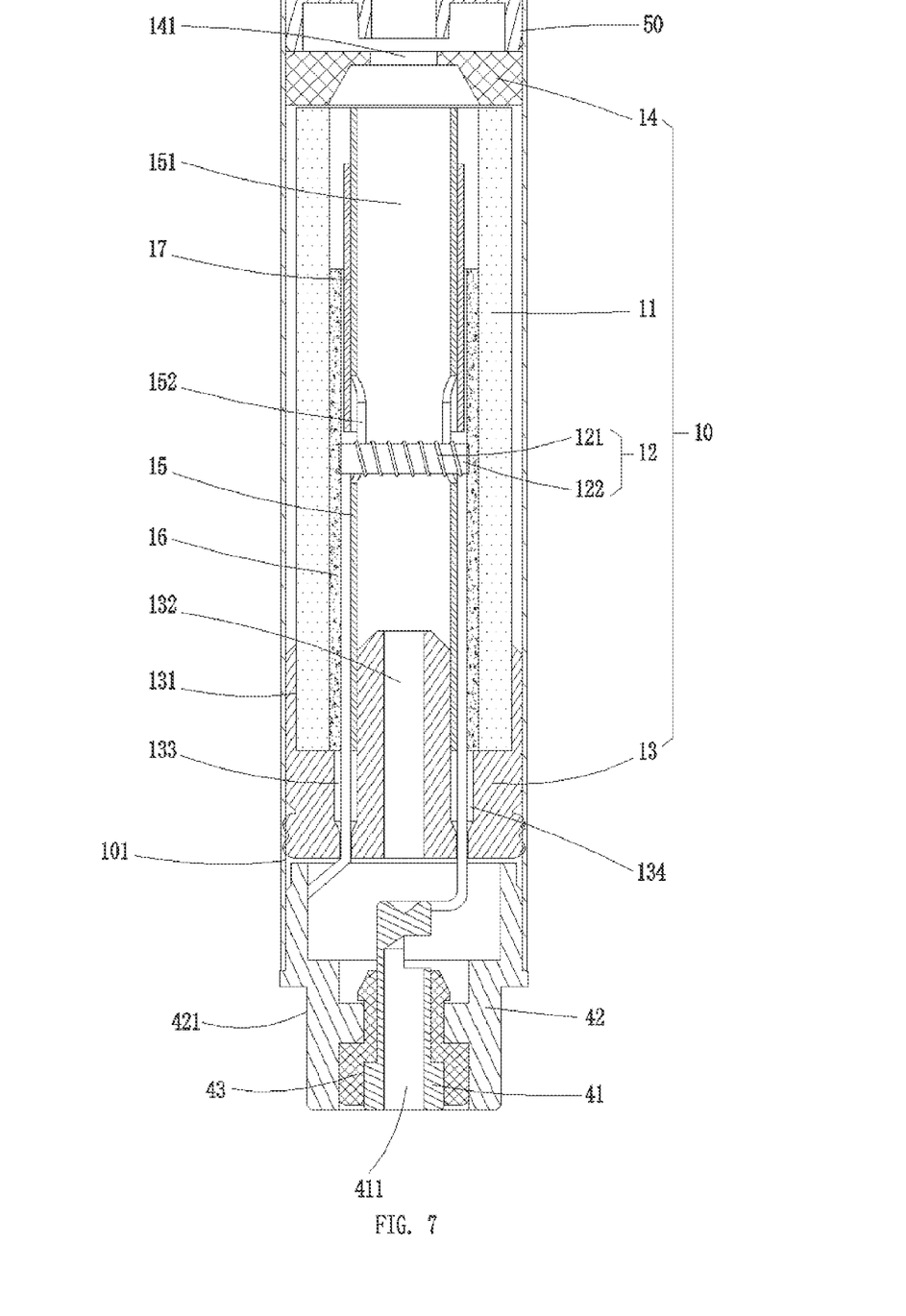
FIG. 7 a cross-sectional view of an inhaling rod of the electronic cigarette in accordance with the embodiment of the present invention.

As shown in FIG. 3, and FIG. 7, the atomizing device 10 comprises a liquid storage component 11, an atomizer 12, an atomizing seat 13 and an atomizing cover 14.

The liquid storage component 11 is capable of absorbing and storing liquid, and is used to absorb and reserve cigarette liquid for vaporization by the atomizer 12. In accordance with this embodiment, the liquid storage component 11 can be made from the materials capable of absorbing and storing liquid such as glass fiber, non-woven fabrics, wood pulp fiber, chemical fiber, polyvinyl alcohol, heat-resistant cotton, chemical -fiber cotton, mixed cotton, liquid-absorbing cotton, foamed nickel, and etc. The liquid storage component 11 is configured as a hollow tube adapted for an inhaling rod 101, and is concentrically fitted in the inhaling rod 101. The inhaling rod 101 as an atomizing casing is used to encapsulate the liquid storage component 11 in accordance with this embodiment, which simplifies whole structure of the electronic cigarette. Certainly, the atomizing device 10 can also be set with an independent atomizing casing instead.

The atomizer 12 is used to vaporize cigarette liquid into vapor mist, comprising electric heating wire 121 and an atomizing rod 122; the electric heating wire 121 winds around the atomizing rod 122, and the atomizing rod 122 is fixedly supported within the liquid storage component 11 so as to absorb cigarette liquid in the liquid storage component 11 for atomization by the electric heating wire 121. The atomizing rod 122 is configured as a cylinder, and is made from heat-resistant and liquid-absorbility materials such as glass fiber or the like.

The atomizing seat 13 and the atomizing cover 14 are respectively set at either end of the liquid storage component 11, by such way to seal and fix the liquid storage component 11 in the inhaling rod 101. As shown in FIG. 7, the atomizing seat 13 defines a slot 131 at its end facing the liquid storage component 11 for holding the liquid storage component 11, centrally defines a first air vent 132 aligned to the center of the liquid storage component 11 for intercommunicating air passage; and the atomizing cover 14 centrally defines a second air vent 141 aligned to the center of the liquid storage component 11 for intercommunicating air passage. The atomizing seat 13 and the atomizing cover 14 are made from rubber materials such as silica gel or the like with an ability of elastic deformation in accordance with this embodiment, both which have exterior profiles adapted for the interior profile of the inhaling rod 101 and preferably engaged with interference fit therebetween, in such way that the atomizing seat 13 and the atomizing cover 14 have their exterior walls tightly fitted in the inhaling rod 101 to seal the liquid storage component 11.

The atomizing seat 13 at its sidewall axially defines a first wire hole 133 and a second wire hole 134 for passing either end of the electric heating wire 121 in this embodiment. The electric heating wire 121 has both ends thereof respectively passing through the first wire hole 133 and the second wire hole 134 to electrically connect with the battery 20.

The liquid storage component 11 is supported and fixed between the atomizing seat 13 and the atomizing cover 14 by a support 15 in this embodiment. The support 15 centrally defines a through hole 151 connecting the first air vent 132 with the second air vent 141 so as to intercommunicate air passage. The through hole 151 is meanwhile used as an atomizing chamber for receiving the atomizer 12 and being provided for the atomizer working therein.

The atomizing rod 122 is radially fixed in the support 15 in accordance with this embodiment, the support 15 at its sidewall defines apertures 152 radially running through its sidewall, the atomizing rod 122 has both ends thereof respectively passing through the apertures 152, extending out of the support 15, and contacting the inner wall of the liquid storage component 11, so as to absorb cigarette liquid in the liquid storage component 11 for vaporization by the electric heating wire 121.

As an embodiment, the atomizing rod 122 can also be axially equipped within the support 15; when the atomizing rod 122 is axially installed, the electric heating wire 121 is desired to fully contact the inner wall of the support 15 for atomization and the support 15 is desired to have its inner through hole 151 intercommunicated with the air passage. It is understood, while the atomizing rod 122 with the electric heating wire 121 is axially fitted within the liquid storage component 11, the liquid storage component 11 can also be supported and fixed between the atomizing seat 13 and the atomizing cover 14 by means of the atomizer 12 instead of the support 15, namely, the support 15 is omitted and not necessarily used. Otherwise, if the electric heating wire 121 is axially installed and can supply enough support force, there is no need to set the atomizing rod 122 in the atomizer 12, while the liquid storage component 11 with the heating wire 121 is supported and fixed within the inhaling rod 101 by the support force from the electric heating wire 121 itself.

Because of high temperature during the electric heating wire 121 is electrified to atomize cigarette liquid, for improving the using life and heat resistance of the liquid storage component 11, a thermally insulating component 16 made from heat-resistant and liquid-absorbility materials is fitted between the liquid storage component 11 and the support 15 in accordance with an embodiment, so as to protect the liquid storage component 11. Herein, both ends of the atomizing rod 122 respectively pass through the apertures 152 of the support 15, and then contact the inner wall of the thermally insulating component 16 (as shown in FIG. 7).

Furthermore, a locating tube 17 is applied around the exterior of the support 15 above or below the atomizing rod 122, and one end of the locating tube 17 abuts against the atomizing rod 122 so that the atomizing rod 122 is tightly fitted in the apertures 152 of the support 15. In this embodiment, for facilitating arrangement of the electric heating wire 121 and space saving, the locating tube 17 is preferably is fitted above the atomizing rod 122.

Referring to FIG. 3, in this embodiment, a second electrode assembly 41 is provided at the end of the atomizing device 10 facing the battery 20 so as to be resiliently contacted by the first electrode assembly 31 for electric connection.

The second electrode 41 is fixed in the main rod 100 via a second connecting seat 42, the second electrode 41 and the second connecting seat 42 are made from metal conductive materials, both two are insulated from each other and respectively connected with either end of the electric heating wire 121 so as to form positive and negative electrodes of the atomizing device 10. Specifically, the second connecting seat 42 interconnects the atomizing seat 13, and both ends of the electric heating wire 121 respectively pass through the first wire hole 133 and the second wire hole 134 and electrically connect the second electrode 41 and the second connecting seat 42. The second connecting seat 42 at its center defines a second electrode chamber 423 (as shown in FIG. 2) which longitudinally runs though from its top to bottom wall, and the second electrode 41 is tightly fitted in the second electrode chamber 423 and insulated from the second connecting seat 42 via a second insulation sleeve 43. The second electrode 41 centrally defines a third air inlet vent 411 intercommunicated with the first air inlet vent 3111 and the second air inlet vent 3121.

As shown in FIG. 3, FIG. 4, and FIG. 7, a top end of the first connecting seat 32 facing the second connecting seat 42 defines a fixing groove 321 so as for receiving and fixing the corresponding end of the second connecting seat 42 therein; the end of the second connecting seat 42 inserted in the first connecting seat 32 is correspondingly configured as an extension 421, and the extension 421 matches the interior profile of the fixing groove 321 so as for being accommodated in the fixing groove 321.

During assembling the electronic cigarette, the extension 421 is disposed in the fixing groove 321, the first connecting seat 32 contacts the second connecting seat 42, and the first electrode assembly 31 resiliently abuts against the second electrode 41. When the first connecting seat 32 and the second connecting seat 42 are apart from each other, an exterior force applied to the first electrode assembly 31 is removed, thus the resilient mechanism 313 takes the electrode 312 to restore its original place.

In this embodiment, the main rod 100 comprises the interconnected inhaling rod 101 and power rod 102 (referring to FIG. 1 and FIG. 3), the atomizing device 10 is equipped within the inhaling rod 101, and the battery 20 is equipped within the power rod 102. The first connecting seat 32 is disposed at the end of the power rod 102 interconnected with the inhaling rod 101, and the second connecting seat 42 is disposed at the end of the inhaling rod 101 interconnected with the power rod 102.

In one embodiment, the power rod 102 and the inhaling rod 101 are configured as being magnetically interconnected, thus the power rod 102 is equipped with a first magnetic part where interconnected with the inhaling rod 101, and the inhaling rod 101 is correspondingly equipped with a second magnetic part attracting the first magnetic part so as to tightly connect the power rod 102.

Because the first connecting seat 32 is set at the end of the power rod 102 near the atomizing device 10, the second connecting seat 42 is set at the end of the inhaling rod 101 near the battery 20, and the first connecting seat 32 is suitably connected with the second connecting seat 42, when arranging the first magnetic part and the second magnetic part, for reducing components and simplifying the structure of the electronic cigarette, the first connecting seat 32 is made from conductive magnet or magnetic materials, thus constitutes the first magnetic part; accordingly, the second connecting seat 42 is made from conductive magnet or magnetic materials, thus constitutes the second magnetic part. Otherwise, an independent part made from conductive magnet or magnetic materials is provided at the corresponding end of the power rod 102 and thus constitutes the first magnetic part; or an independent part made from conductive magnet or magnetic materials is provided at the corresponding end of the inhaling rod 102 and thus constitutes the second magnetic part.

Referring to FIG. 2, in this embodiment, the second magnetic part is constituted by the second connecting seat 42 which is made from conductive material, and the first magnetic part is configured as a permanent magnet 34 disposed in the first connecting seat 32. Referring to FIG. 4, a flange 322 is formed on the interior wall of the first connecting seat 32 where the first electrode cavity 323 joins the fixing groove 321, and the permanent magnet 34 is tightly abutted under the flange 322 and insulated from the first electrode assembly 31 by the first insulation sleeve 33. The permanent magnet 34 substantially shaped as a hollow annular column, is radially and tightly fitted between the first connecting seat 32 and the first insulation sleeve 33, and is longitudinally secured between the flange 322 of the first connecting seat 32 and the top wall 334 of the first insulation sleeve 33; and further together with the engagement between the cutout 336 of the first insulation sleeve 33 and the extending flange 325 of the first connecting seat 32, therefore, the first insulation sleeve 33 bearing the permanent magnet 34 thereon and encasing the first electrode assembly 31 therein is tightly mounted within the first connecting seat 32.

To avoid a gap existing where the inhaling rod 101 is connected with the power rod 102 due to the interconnection not tightly enough between the first connecting seat 32 and the second connecting seat 42, the axial depth of the fixing groove 321 in the first connecting seat 32 is slightly greater than the axial length of the extension 421 of the second connecting seat 42, so that when the extension 421 is inserted in fixing groove 321, the extension 421 can keep a certain distance from the permanent magnet 34 while attracted by the permanent magnet 34, thereby, there is no gap at the interconnection of the inhaling rod 101 and the power rod 102, and a clean and attractive appearance of the electronic cigarette is obtained.

As an embodiment, the inhaling rod 101 and the power rod 102 can be interconnected by means of threaded connection, clamping connection or the like; for example, the first connecting seat 32 and the second connecting seat 42 at their joins respectively forms exterior threads and interior threads matching with each other so as to obtain a threaded connection therebetween.

As shown in FIG. 1 to FIG. 3, the electronic cigarette is set with a mouthpiece 50 at its end away from the battery 20; the mouthpiece 50 is separated from the inhaling rod 101, and the mouthpiece 50 centrally defines an air-puffing hole. As one embodiment, the mouthpiece 50 and the atomizing casing 101 may be molded in one piece as well. The mouthpiece 50 is shaped as flat cylinder in accordance with the embodiment, it is understood, the mouthpiece 50 may be shaped as a tube adapted for the inhaling rod 101 as well; or, is shaped as a tempered cartridge with a diameter gradually reduced to its end.

As shown in FIG. 2 and FIG. 3, the electronic cigarette further comprises an atomization-control unit, the atomization-control unit is respectively electronically connected with both the battery 20 and the atomizing device 10, so as to control the atomizing device 10 being electrically connected or disconnected. The atomization-control unit can be set between the atomizing device 10 and the battery 20, or at an end of the battery 20 away from the atomizing device 10.

In this embodiment, the atomization-control unit is preferably set at the end of the battery 20 away from the atomizing device 10, and comprises an atomization-control circuit and an atomization-control switch which is electrically connected with the atomization-control circuit.

In this embodiment, the atomization-control switch preferably uses a sensor switch 61 (referring to FIG. 3), and the sensor switch 61 is mounted in the power rod 102 by means of a switch holder 62. Specifically, in this embodiment, the sensor switch 61 is a kind of capacitive sensor switch, when the user smokes by the electronic cigarette, the capacitive sensor switch senses a change of capacitance due to inhaling air, and then controls the atomization-control circuit to switch on to enable the electronic cigarette working. As an embodiment, the sensor switch 61 may also be an airflow sensor switch, when the user inhales at the mouthpiece end of the main rod 101, the cavity within the electronic cigarette produces negative pressure which enables the airflow sensor switch produce pulsing signal so as to control the atomization-control circuit to switch on.

Since the sensor switch 61 is precisely manufactured, and is often equipped with a special controller therein, so, in this embodiment, the atomization-control circuit may be directly integrated in the controller of the sensor switch 61. As an embodiment, the atomization-control circuit may also be integrated in a sensor-control circuit board which is independent from the sensor switch 61 and respectively electrically connected with the sensor switch 61 and the battery 20.

As an embodiment, the atomization-control switch may also be a traditional key switch, the key switch controls the circuit board to be electrically connected with the battery 20 by means of a key so as to control the atomization-control circuit further to control the atomizing device 10 switch on or off by means of the key operation.

Referring to FIGS. 2 to 3, the power rod 102 at its end away from the inhaling rod 101 is set with a light emitting device, the light emitting device is used as an indicator of the electronic cigarette working, comprising light emitting unit electrically connected with the battery 20 and a light cap 70 disposed in the corresponding end of the power rod 102; and the light cap 70 is used for the light emitting unit to transmit lights. In this embodiment, the light emitting unit is a red luminescent lamp, so that when the user smokes by the electronic cigarette, a red ring resembling tobacco burning is available at the end of the electronic cigarette away from the mouthpiece 50, which improves the reality of the use's sense and vision. The light cap 70 is wholly or at least its top face transparent or semitransparent, so as for the light emitting unit to transmit lights therethrough.

As following, the battery 20 has one end electrically connected with the electrode assembly 31 as its positive pole, and has the other end electrically connected with the first connecting seat 32 as the negative pole, and the atomization-control switch is the sensor switch 61 as the example, the electric current direction in the electronic cigarette is detailed described.

The users smokes by the electronic cigarette, the sensor switch 61 senses and switches on the atomization-control circuit, the detail electric current direction is that: current from the positive pole of the battery 20 to the first electrode assembly 31, then through the second electrode 41 into the positive electrode of the electric heating wire 121, then flows into the negative electrode of the electric heating wire 121 to the second connecting seat 42, and finally through the first connecting seat 32 back to the negative pole of the battery 20.

It is understood, the electronic cigarette in accordance with embodiments of the present invention is not limited in the embodiments of FIGS. 1 to 7, new embodiments can be obtain by combining technical characters in all above embodiments.

The above embodiment is only to illustrate the mode of the invention. Spirit of variations or modifications made to the equivalent, should be covered within the scope of the present invention.

What is claimed is:

1. An electronic cigarette, comprising an atomizing device for vaporizing cigarette liquid, a battery electrically connected with the atomizing device, and a first electrode assembly disposed between the battery and the atomizing device; wherein the first electrode assembly comprises a first electrode seat, a first electrode and a resilient mechanism; the first electrode seat is electrically connected with the battery; the first electrode resiliently engaged with a second electrode of the atomizing device by means of the resilient mechanism, and the resilient mechanism is resiliently connected between the first electrode seat and the first electrode; the first electrode seat and the first electrode respectively define a first air inlet vent and a second air inlet vent for intercommunicating an air passage of the electronic cigarette; the electronic cigarette comprises a main rod; the first electrode assembly is mounted within the main rod by means of a first connecting seat the second electrode is fixed in the main rod by means of a second connecting seat;

the first connecting seat is made from magnet or magnetic material to form the first magnetic part, or is provided with an independent component made from conductive magnet or magnetic material to form the first magnetic part;

the second connecting seat is made from magnet or magnetic material to form the second magnetic part, or is provided with an independent component made from conductive magnet or magnetic material to form the second magnetic part;

the independent component made from conductive magnet or magnetic material is a permanent magnet.

2. The electronic cigarette according to claim 1, wherein the first electrode seat defines a cavity, the first electrode is set in an open end of the cavity, the open end inwards and radially extends to form an interior baffle ring; one end of the electrode disposed in the cavity radially and outwards extends to form an exterior baffle ring engaged with the interior baffle ring, and the other end thereof extending outwards from the cavity under an action of the resilient mechanism.

3. The electronic cigarette according to claim 2, wherein either end of the resilient mechanism are respectively fixed and electrically connected with the first electrode seat and the first electrode.

4. The electronic cigarette according to claim 1, wherein the resilient mechanism is a compressible spring or spring plate electrically connected with the first electrode seat and the first electrode.

5. The electronic cigarette according to claim 1, wherein the resilient mechanism is configured as two mutually-repelled magnets respectively disposed at the first electrode seat and the first electrode.

6. The electronic cigarette according to claim 1, wherein the resilient mechanism is an airbag.

7. An electronic cigarette, comprising an atomizing device for vaporizing cigarette liquid, a battery electrically connected with the atomizing device, and a first electrode assembly disposed between the battery and the atomizing device; wherein the first electrode assembly comprises a first electrode seat, a first electrode and a resilient mechanism;

the first electrode seat is electrically connected with the battery; the first electrode resiliently engaged with a second electrode of the atomizing device by means of the resilient mechanism, and the resilient mechanism is resiliently connected between the first electrode seat and the first electrode;

the electronic cigarette comprises a main rod, the first electrode assembly is mounted within the main rod by means of a first connecting seat; the first connecting seat centrally defines a first electrode chamber which longitudinally runs through from its top to bottom end; the first electrode assembly is tightly fitted in the first electrode chamber via a first insulation sleeve; and the first connecting seat is made from conductive material and is insulated from the first electrode assembly; and the second electrode is fixed in the main rod by means of a second connecting seat; the second electrode is tightly fitted in the second connecting seat by means of a second insulation sleeve;

the atomizing device has an electric heating wire; and the second electrode which is resiliently contacted by the first electrode, is disposed at an end of the atomizing device opposite to the battery;

the second connecting seat centrally defines a second electrode chamber which longitudinally runs through its top to bottom end; the second electrode is tightly fitted in the second electrode chamber by means of the second insulation sleeve; the second connecting seat is made from conductive material; the second electrode and the second connecting seat are insulated from each other, and respectively connected with either end of the electric heating wire to form positive and negative electrodes of the atomizing device;

one end of the first connecting seat facing the second connecting seat is configured as a fixing groove for receiving a corresponding end of the second connecting seat, and the corresponding end of the second connecting seat forms an extension matching an interior profile of the fixing groove whereby being received in the fixing groove.

8. The electronic cigarette according to claim 7, wherein the main rod comprises a power rod and an inhaling rod interconnected; the battery is set in the power rod, the atomizing device is set in the inhaling rod, the first connecting seat is set in one end of the power rod where the inhaling rod is interconnected, the second connecting seat is set in one end of the inhaling rod where the power rod is interconnected.

9. The electronic cigarette according to claim 8, wherein the power rod and the inhaling rod are magnetically connected, the power rod is provided with a first magnetic part where the inhaling rod is connected, the inhaling rod is correspondingly provided with a second magnetic part for magnetically attracting the first magnetic part whereby to tightly connect the power rod.

10. The electronic cigarette according to claim 9, wherein the first connecting seat is made from magnet or magnetic material to form the first magnetic part, or a corresponding end of the power rod is provided with an independent component made from conductive magnet or magnetic material to form the first magnetic part; the second connecting seat is made from magnet or magnetic material to form the second magnetic part, or a corresponding end of the inhaling rod is provided with an independent component made from conductive magnet or magnetic material to form the second magnetic part.

11. The electronic cigarette according to claim 10, wherein the first magnetic part is a permanent magnet; a flange is formed where the first electrode chamber is joined with the fixing groove, the permanent magnet abuts against the flange via the first insulated sleeve and is insulated from the first electrode assembly.

12. An electronic cigarette comprising:
an inhaling rod; and
a power rod electrically connected with the inhaling rod;
wherein the inhaling rod and the power rod are resiliently engaged with each other by means of a resilient connecting means; the resilient connecting means comprises a first electrode assembly and a second electrode electrically interconnected; the first electrode assembly comprises a first electrode, a first electrode seat, and a resilient mechanism; the resilient mechanism is resiliently and electrically fixed between the first electrode seat and the first electrode, and the first electrode is resiliently engaged with the second electrode under a resilient action of the resilient mechanism; and
the power rod and the inhaling rod are magnetically connected.

13. The electronic cigarette according to claim 12, wherein the first electrode seat is a hollow cylinder with a cavity therein, the first electrode and the resilient mechanism are coaxially accommodated in the cavity; the first electrode movably extends upwards from a top open end of the electrode seat; and the resilient mechanism abuts under the first electrode.

14. The electronic cigarette according to claim 13, wherein the first electrode is substantially a hollow cylinder with an exterior baffle ring therearound, the first electrode seat forms an interior baffle ring at the open end thereof for matching the exterior baffle ring of the first electrode, whereby the first electrode is able to be limited by means of the engagement between the interior and exterior baffle rings under the resilient action of the resilient mechanism; and the resilient mechanism is a compressible spring or spring plate electrically connected with the first electrode seat and the first electrode.

15. The electronic cigarette according to claim 12, wherein the first electrode assembly is tightly fitted within the power rod via a first insulation sleeve; the first insulation sleeve comprises a hollow cylindrical base tightly fitted within the power rod, the cylindrical base at its top wall axially forms a hollow cylindrical extension with a relatively smaller diameter tightly holding the first electrode assembly therein;

an annular magnet is fitted around the cylindrical extension of the first insulation sleeve and is tightly fitted within the power rod whereby the inhaling rod is magnetically connected with the power rod; the first electrode seat forms an exterior annular flange therearound, a top section of the first electrode seat is tightly fitted within the cylindrical extension of the first insulation sleeve with its exterior annular flange abutting against an inner of the top wall of the first insulation sleeve.

16. The electronic cigarette according to claim 12, wherein the first electrode assembly is mounted within the inhaling rod by means of a first connecting seat;

the second electrode is fixed in the power rod by means of a second connecting seat;

the first connecting seat is made from magnet or magnetic material to form the first magnetic part, or a corresponding end of the power rod is provided with an independent component made from conductive magnet or magnetic material to form the first magnetic part;

the second connecting seat is made from magnet or magnetic material to form the second magnetic part, or a corresponding end of the inhaling rod is provided with an independent component made from conductive magnet or magnetic material to form the second magnetic part;

the independent component made from conductive magnet or magnetic material is a permanent magnet.

* * * * *